US010282516B2

(12) United States Patent
Larcom et al.

(10) Patent No.: US 10,282,516 B2
(45) Date of Patent: May 7, 2019

(54) MEDICAL IMAGING REFERENCE RETRIEVAL

(71) Applicant: Konica Minolta Laboratory U.S.A., Inc., San Mateo, CA (US)

(72) Inventors: Ronald Larcom, San Jose, CA (US); Shinsuke Katsuhara, Foster City, CA (US); Satoshi Kasai, San Jose, CA (US)

(73) Assignee: Konica Minolta Laboratory U.S.A., Inc., San Mateo, CA (US)

( * ) Notice: Subject to any disclaimer, the term of this patent is extended or adjusted under 35 U.S.C. 154(b) by 907 days.

(21) Appl. No.: 14/657,897

(22) Filed: Mar. 13, 2015

(65) Prior Publication Data

US 2016/0267221 A1 Sep. 15, 2016

(51) Int. Cl.
*G06Q 50/00* (2012.01)
*G06F 19/00* (2018.01)
(Continued)

(52) U.S. Cl.
CPC .......... *G06F 19/321* (2013.01); *G06F 16/583* (2019.01); *G06F 19/00* (2013.01); *G16H 10/60* (2018.01); *G16H 50/70* (2018.01)

(58) Field of Classification Search
CPC .......... A61N 1/08; G06F 17/30; G06F 19/30; G06F 19/32; G06F 19/321; G06F 19/324;
(Continued)

(56) References Cited

U.S. PATENT DOCUMENTS 7,374,077 B2   5/2008  Shimura
8,934,695 B2   1/2015  Sato et al.
(Continued)

FOREIGN PATENT DOCUMENTS

JP   2013200590 A   10/2013
JP   2014029644 A    2/2014
(Continued)

OTHER PUBLICATIONS

Hardie et al. "Performance Analysis of a New Computer Aided Detection System for Identifying Lung Nodules on Chest Radiographs." Medical Image Analysis 12 (2008): 240-58.
(Continued)

*Primary Examiner* — Tran N Nguyen
(74) *Attorney, Agent, or Firm* — Osha Liang LLP

(57) ABSTRACT

A method for managing a patient medical case. The method includes: identifying, within a patient medical image of the patient medical case, a first abnormal image region; retrieving, from a reference medical case (RMC) repository and before the patient medical image is displayed to a user, a first set of reference medical cases including reference medical images matching the first abnormal image region; displaying, within a GUI, the patient medical image and at least one of the first set of reference medical cases to the user; receiving, from the user after the patient medical image is displayed, a selection of a second abnormal image region within the patient medical image; retrieving, from the RMC repository, a second set of reference medical cases including reference medical images matching the second abnormal image region; and displaying, with the GUI, at least one of the second set of reference medical cases.

14 Claims, 6 Drawing Sheets

(51) Int. Cl.
*G16H 10/60* (2018.01)
*G16H 50/70* (2018.01)
*G06F 16/583* (2019.01)
*G06Q 10/00* (2012.01)

(58) Field of Classification Search
CPC .... G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06Q 10/10; G06Q 40/08; G06Q 50/22; G06Q 50/24; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/40; G16H 70/60; G16H 80/00

See application file for complete search history.

(56) References Cited

U.S. PATENT DOCUMENTS

| 2005/0102315 | A1* | 5/2005 | Krishnan | G06T 7/0012 |
| 2009/0307170 | A1* | 12/2009 | Jordan | G06N 5/04 |
| | | | | 706/47 |
| 2014/0321773 | A1 | 10/2014 | Hammon et al. | |
| 2014/0379364 | A1 | 12/2014 | Liu et al. | |

FOREIGN PATENT DOCUMENTS

| WO | 2009060355 A1 | 5/2009 |
| WO | 2013018363 A1 | 2/2013 |

OTHER PUBLICATIONS

Schilham et al. "A Computer-aided Diagnosis System for Detection of Lung Nodules in Chest Radiographs with an Evaluation on a Public Database." Medical Image Analysis 10 (2006): 247-58.

* cited by examiner

MEDICAL IMAGING REFERENCE RETRIEVAL

BACKGROUND

Medical imaging (e.g., X-ray images) is commonly used by medical professionals for diagnostic purposes. In other words, one or more medical professionals may analyze and interpret a patient's medical image in order to diagnose the patient's illness/injury. This analysis/interpretation may require the medical professional to compare the patient's medical image with medical images from previous patients (i.e., existing medical images) in order to correctly diagnose the current patient's illness/injury.

However, these comparisons are very time consuming for the medical professional. The medical professional must first locate the appropriate existing medical images and then perform the comparison. Regardless, these comparisons are desirable because they lead to more accurate diagnoses. Accordingly, tools that help increase the efficiency of medical professionals analyzing and interpreting medical images are desirable.

SUMMARY

In general, in one aspect, the invention relates to a method for managing a patient medical case. The method comprises: identifying, within a patient medical image of the patient medical case, a first abnormal image region; retrieving, from a reference medical case repository and before the patient medical image is displayed to a first user, a first plurality of reference medical cases comprising a first plurality of reference medical images matching the first abnormal image region; displaying, within a graphical user interface (GUI), the patient medical image and at least one of the first plurality of reference medical cases to the first user; receiving, from the first user after the patient medical image is displayed, a selection of a second abnormal image region within the patient medical image; retrieving, from the reference medical case repository, a second plurality of reference medical cases comprising a second plurality of reference medical images matching the second abnormal image region; and displaying, with the GUI, at least one of the second plurality of reference medical cases.

In general, in one aspect, the invention relates to a system for managing a patient medical case. The system comprises: a computer processor; a reference medical case repository; a reference case identification engine (RCIE), executing on the computer processor, and configured to: identify, within a patient medical image of the patient medical case, a first abnormal image region; retrieve, from a reference medical case repository and before the patient medical image is displayed to a first user, a first plurality of reference medical cases comprising a first plurality of reference medical images matching the first abnormal image region; and retrieve, from the reference medical case repository, a second plurality of reference medical cases comprising a second plurality of reference medical images matching a second abnormal region; and a graphical user interface (GUI) configured to display the patient medical image and at least one of the first plurality of reference medical cases to the first user; receive, from the first user after the patient medical image is displayed, a selection of the second abnormal image region within the patient medical image; and display at least one of the second plurality of reference medical cases.

In general, in one aspect, the invention relates to a non-transitory computer readable medium (CRM) storing instructions for managing a patient medical case. The instructions comprise functionality for identifying, within a patient medical image of the patient medical case, a first abnormal image region; retrieving, from a reference medical case repository and before the patient medical image is displayed to a first user, a first plurality of reference medical cases comprising a first plurality of reference medical images matching the first abnormal image region; displaying, within a graphical user interface (GUI), the patient medical image and at least one of the first plurality of reference medical cases to the first user; receiving, from the first user after the patient medical image is displayed, a selection of a second abnormal image region within the patient medical image; retrieving, from the reference medical case repository, a second plurality of reference medical cases comprising a second plurality of reference medical images matching the second abnormal image region; and displaying, with the GUI, at least one of the second plurality of reference medical cases.

DETAILED DESCRIPTION

Figure 1:
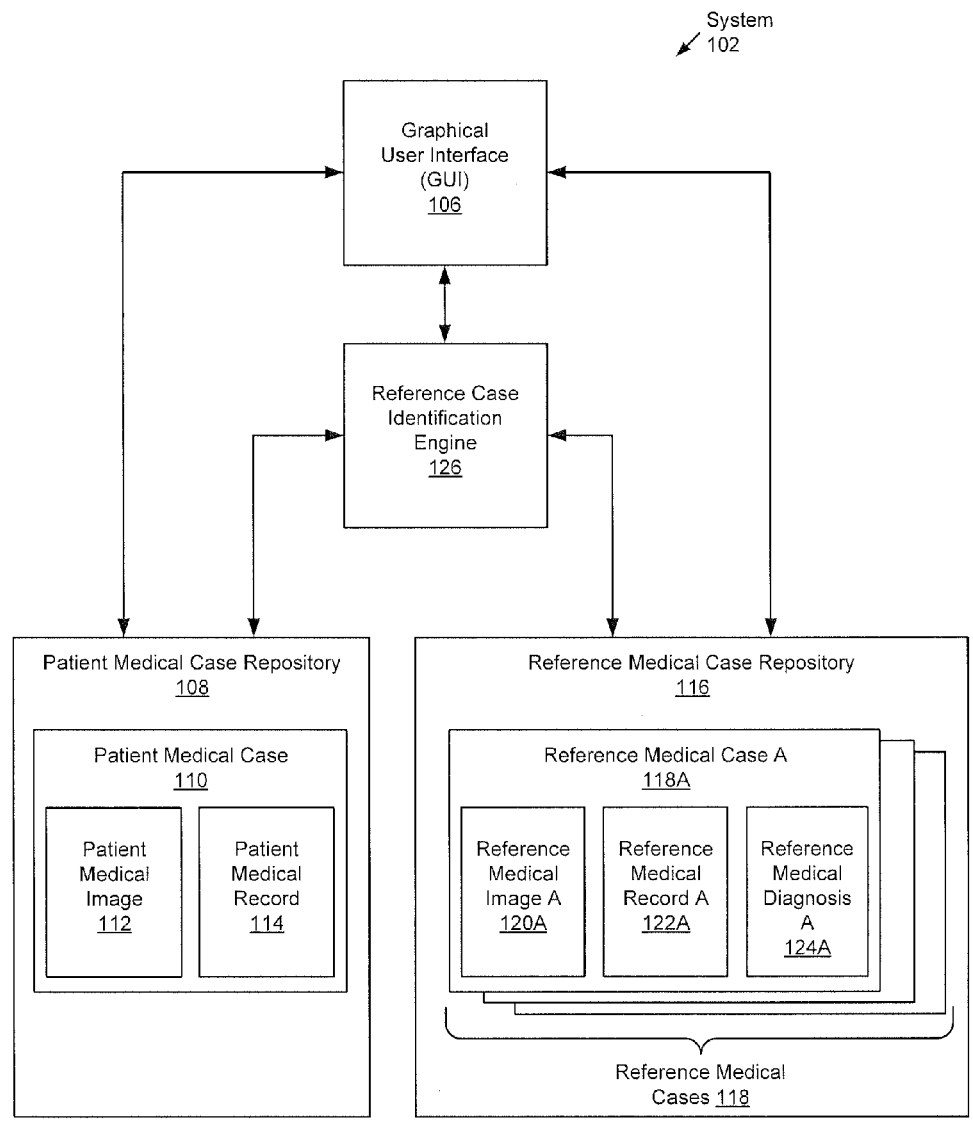
FIG. 1 shows a schematic diagram of a system in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

A wide range of medical imaging methods such as, for example, X-ray radiography, magnetic resonance imaging and ultrasonography are used in modern medicine to create visual representations of the interior of a body for clinical analysis and medical intervention. A medical professional examines medical images obtained from a patient in view of other previously diagnosed patient cases to guide making and/or confirming a diagnosis.

Embodiments of the invention provide a method, a system, and a non-transitory computer readable medium (CRM) for managing a patient medical case. The patient medical case may include a patient medical image accompanied by a patient medical record that provides additional information such as, for example, patient demographics and clinical information.

In one or more embodiments of the invention, reference medical cases with similarities to the patient medical case are obtained from a reference medical case repository.

In one or more embodiments of the invention, reference medical cases that are similar to the patient medical case are identified using a two-stage process. In the first stage, abnormalities in the patient medical image are automatically identified/detected and reference patient medical cases having reference medical images that match the identified/detected abnormality are retrieved. This first stage may be executed before the medical professional examines the patient medical image. Moreover, one or more of the similar reference patient medical cases may be displayed with the patient medical image during the examination of the patient medical image.

In one or more embodiments, in the second stage, abnormalities in the patient medical image are manually selected by the medical professional and reference patient medical cases having reference medical images that match the manually selected abnormality are retrieved and displayed.

Each reference medical case includes a reference medical image, a reference medical diagnosis, and a reference medical record that includes, for example, patient demographics and other reference case-related information. A subset of the identified reference medical cases is displayed to the user (i.e., medical professional) that interprets the patient medical image. The user may rely on the reference medical diagnoses associated with the reference medical cases that are displayed for diagnostic guidance and/or to confirm a diagnosis.

FIG. 1 shows a system (102) in accordance with one or more embodiments of the invention. As shown in FIG. 1, the system (102) has multiple components, including a graphical user interface (GUI) (106), a patient medical case repository (108), a reference medical case repository (116), and a reference case identification engine (126). Each of these components may be located on the same computing device (e.g., desktop computer, server, laptop computer, tablet computer, smart phone, radiology computer workstation, etc.) or may be located on different computing devices connect by a network of any size having wired and/or wireless segments.

In one or more embodiments of the invention, the system (102) includes the GUI (106). The GUI (106) is configured to display a patient medical image (112), a patient medical record (114), reference medical images (120), reference medical records (122), and reference medical diagnoses (124) to a user within the same or different windows. Further, the GUI (106) is configured to accept user input using one or more GUI widgets (e.g., radio buttons, drop-down lists, textboxes, etc.), thus enabling the user to interact with the displayed content. The user may, for example, select a different patient and/or reference case for display. The user may further manipulate the displayed medical images. The user may, for example, zoom into a medical image, rotate the medical image, and/or the user may manually select a region of interest. In addition, the user may explore and display medical records and/or diagnoses.

In one or more embodiments of the invention, the system includes the patient medical case repository (108). The patient medical case repository (108) stores multiple patient medical cases (e.g., patient medical case (110)). The patient medical case repository (108) may be, for example, a directory on a local or remote storage device where the patient medical cases are stored, or it may be a database designed to accommodate a number of patient medical cases, for example in a picture archiving and communication system (PACS).

In one or more embodiments of the invention, the patient medical case (110) includes a patient medical image (112) and a patient medical record (114). The patient medical image (112) may be stored in any type of format (e.g., GIF, JPEG, TIFF, etc.) including formats that utilize lossy or lossless compression. The patient medical image may have been generated using any type of imaging modality including, for example, an X-ray, magnetic resonance imaging (MRI), ultrasound, computed tomography (CT), or a positron emission tomography (PET) device. Depending on the imaging study performed and the imaging modality used, the content of the patient medical image may be different. An X-ray patient medical image, for example, may show parts of the skeletal system, whereas a set of MRI medical images may show a slice of the brain. Further, depending on the imaging study performed, and the imaging modality used, the resolution and size of the patient medical image me be different.

In one or more embodiments of the invention, the patient medical image (112) may be stored using the Digital Imaging and Communications in Medicine (DICOM) format. The DICOM standard defines file format and network communication protocol for seamless interaction of different medical imaging modalities (e.g., computed tomography (CT), magnetic resonance (MR), and ultrasound devices) of different manufacturers. A DICOM file may be used to store the patient medical image (112) along with accompanying metadata that provides a comprehensive description of the performed medical image procedure and other patient medical case-related information. This information may be stored in the patient medical record (114).

In one or more embodiments of the invention, the patient medical record (114) may include a description of the patient medical image (112). The patient medical record (114) may include, for example, the parameters used to obtain the patient medical image (112) (i.e., the settings of the imaging device when the patient medical image (112) was generated). The patient medical record (114) may further include demographic information, the patient's symptoms, other clinical information and history, clinical vital signs, etc. The patient medical record (114) may be stored, along with the patient medical image (112) in the same repository, or it may be stored in a separate local or remote repository. In one or more embodiments of the invention, the information in the patient medical record (114) may be derived from the metadata in the DICOM file used to store the patient medical image (112). Alternatively, the patient medical record (114) may be the metadata in the DICOM file that stores the patient medical image (112).

In one or more embodiments of the invention, additional patient medical record information may be obtained from an electronic order used to request the patient medical image (112). This electronic order may be consistent with the HL7 ORM-O01 standard. HL7 is a standard accredited by the American National Standards Institute (ANSI) that was designed in order to provide a comprehensive framework for the exchange, integration, sharing, and retrieval of electronic health information to support clinical practice and the management, delivery and evaluation of health services. The HL7 ORM-O01 electronic order may include, for example, patient name and insurance information, patient demographics (e.g., age, sex, race, place of birth, ambulatory status, smoking/drug use), clinical information (e.g., symptoms), clinical vital signs (e.g., temperature, pulse, blood pressure, blood panels), clinical history (e.g., past surgeries, allergies). The information in the HL7 ORM-O01 order message may partially overlap with the information of the DICOM file metadata, but it may also provide additional patient information. In one or more embodiments of the invention, the information in the electronic order may be added to the patient medical record (114).

In one or more embodiments of the invention, the system includes the reference medical case repository (116). The reference medical case repository (116) stores multiple reference medical cases (118). Each reference medical case includes a reference medical image, a reference medical record, and a reference medical diagnosis. For example, reference medical case A (118A) includes reference medical image A (120A), reference medical record A (122A), and reference medical diagnosis A (124A). The reference medical case repository (116) may be, for example, a searchable database designed to accommodate a number of reference medical cases, for example in a PACS. The reference medical case repository (116) may be provided and maintained by a healthcare provider (e.g., a hospital), or it may be a shared resource that is provided and maintained by a $3^{rd}$ party (e.g., a university, commercial provider, a medical insurance company, etc.).

In one or more embodiments of the invention, the reference medical case repository (116) includes reference medical images that were obtained from reference subjects (i.e., prior subjects or patients). These reference medical images cover any number of body regions and/or organs. Moreover, the reference medical case repository (116) includes reference medical images obtained using various imaging modalities.

In one or more embodiments of the invention, the reference medical record A (122A) of the reference medical case A (120A) may be a complete documentation of a reference subject's (i.e. prior patient's) case. The reference medical record A (122A) may include the reference subject's demographic information, the reference subject's symptoms, other clinical information and history, clinical vital signs, and any other information that may be potentially relevant in context of the reference medical image A (120A) and the reference medical diagnosis A (124A). In one or more embodiments of the invention, certain elements may have been removed from the reference medical record A (122A). For example, the reference medical record may have been redacted to anonymize the reference medical record A (122A). Accordingly, the subject's name, social security number, insurance data, etc. may have been removed. The reference medical record A (122A) may be stored, along with the reference medical image A (120A) and the reference medical diagnosis A (124A) as a reference medical case A (118A) in the reference medical case repository (116).

In one or more embodiments of the invention, the reference medical case A (118A) further includes the reference medical diagnosis A (124A). The reference medical diagnosis A (124A) was made by an experienced medical professional under consideration of the content of the reference medical image A (120A) and the corresponding reference medical record A (122A).

In one or more embodiments of the invention, the reference medical case repository (116) may include reference medical cases (118) covering many different diagnoses, even multiple diagnoses for a single body region or single organ. For example, the reference medical case repository (116) may include multiple reference medical cases (118) having reference medical images that are all X-ray images of lungs with nodules. However, the reference medical diagnosis in one reference medical case may be tuberculosis, i.e., an infection. The reference medical diagnosis in another reference medical case may be a hamartoma, i.e., a benign tumor. The reference medical diagnosis in yet another case may be lymphoma, i.e., a malignant tumor.

In one or more embodiments of the invention, the reference medical case repository (116) may include multiple reference medical cases (118) with the same reference medical diagnosis. For example, the medical reference medical case repository (116) may include multiple reference medical cases (118) with a "lymphoma" reference medical diagnosis. Although these reference medical cases (118) have the same "lymphoma" reference medical diagnosis, the reference medical images of these reference medical cases (118) may differ. For example, the number of nodules in the reference medical images may differ, the size, shape, edge, or any other feature that may characterize lymphomas may differ. Further, the reference medical case repository may also include multiple reference medical cases (118) that are similar, i.e., where the reference medical images and the reference medical diagnosis are similar.

In one or more embodiments of the invention, the reference medical case repository (116) may include reference medical cases (118) where the content of the associated reference medical records is different. For example, the reference subjects from whom the reference medical cases (118) were obtained may belong to different age groups, may include male and female subjects, smokers and non-smokers, etc.

In one or more embodiments of the invention, the reference medical case repository (116) may further include reference medical cases (118) of healthy individuals without diagnosed abnormalities. The associated reference medical images (120), obtained from healthy individuals, may therefore not contain abnormalities.

In one or more embodiments of the invention, the system (102) includes the reference case identification engine (126). The reference case identification engine (126) is configured to identify one or more abnormal image regions in the patient medical image (112). The reference case identification engine (126) is also configured to search the reference medical case repository (116) for reference medical cases (118) with reference medical images that match the one or more abnormal image regions identified in the patient medical image (112). This search may also use information (e.g., age, gender, etc.) from the patient medical record (114) to identify matching reference medical images.

Figure 2A:
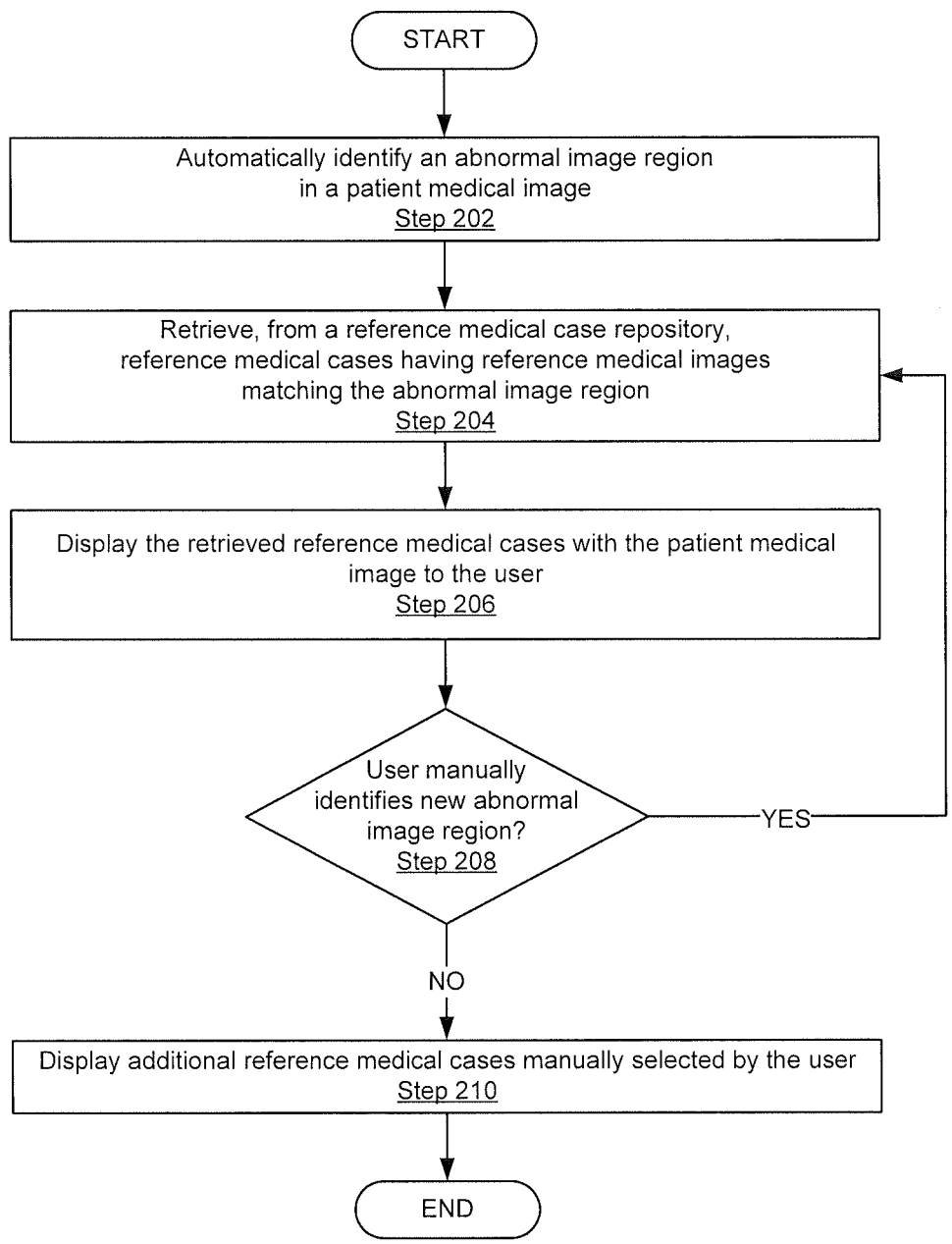
FIGS. 2A and 2B show flowcharts in accordance with one or more embodiments of the invention.

In one or more embodiments of the invention, the reference case identification engine (126) is configured to calculate confidence values for each reference medical case having a matching reference medical image. Moreover, the reference case identification engine (126) is configured to select, from the identified reference medical cases having matching reference medical images, a subset of reference medical cases to be presented to the user via GUI (106). The reference case identification engine (126) is configured to perform this selection under consideration of image content similarity (i.e., similarity between patient medical image (112) and reference medical image A (120A)) and representational coverage of different diagnoses, thus ensuring that all reference medical diagnoses that may be supported by the patient medical image (112) and the patient medical record (114) are presented to the user of the system (102). The details of this process are described below, in reference to FIG. 2.

While FIG. 1 shows a configuration of components, other configurations may be used without departing from the scope of the invention. For example, various components may be combined to create a single component. As another example, the functionality performed by a single component may be performed by two or more components.

FIG. 2 shows a flowchart in accordance with one or more embodiments of the invention. The process depicted in FIG. 2 may be used to manage a patient medical case. Additionally, the process depicted in FIG. 2 may be used to retrieve reference medical cases that are related to the patient medical case. One or more of the steps in FIG. 2 may be performed by the components of the system (102), discussed above in reference to FIG. 1. In one or more embodiments of the invention, one or more of the steps shown in FIG. 2 may be omitted, repeated, and/or performed in a different order than the order shown in FIG. 2. Accordingly, the scope of the invention should not be considered limited to the specific arrangement of steps shown in FIG. 2.

Initially, a patient medical image and an associated patient medical record are obtained. The patient medical image and the associated patient medical record may be obtained from a patient medical case repository, located, for example, on a PACS server. Alternatively, the new medical image may be transmitted from a medical imaging device, for example, an X-ray machine. The patient medical image may be in DICOM format, and may therefore include additional metadata that may be included in the patient medical record. Additional patient-related information may have been received via the electronic order (e.g., a HL7 ORM-O01) that was placed to request the imaging study to be performed on the patient. The patient-related information in the electronic order may also be included in the patient medical record.

In Step 202, one or more abnormal image regions are automatically identified (i.e., using one or more image processing algorithms) in the patient medical image. An abnormal image region may be a single abnormality, or multiple abnormalities that may be clustered in a single region and/or that may be distributed over a larger region in the patient medical image. An abnormal image region is an image region that detectably deviates from the surrounding area within the patient medical image, and where the deviation is unexpected. In one or more embodiments of the invention, abnormal image regions may be detected using computer-aided detection. First, the patient medical image is preprocessed by, for example, resampling for a certain pixel spacing, normalizing for contrast, etc. Next, a model-based approach such as active shape model (ASM) segmentation may be used to isolate the desired body region or organ for further analysis. For example, lungs may be isolated in a thorax image. Subsequently, the isolated image area is analyzed for abnormal image regions. In one or more embodiments of the invention, abnormal image regions may be image regions where pixel data deviates from pixel data in the surrounding area. In a grayscale image, for example, an abnormal image region may be an image region with a higher luminance (i.e., brightness) than the surrounding area. Such abnormal image regions may be detected, for example, by applying a 2D filter kernel, thresholding, template matching, etc. Alternatively, abnormal image regions may be detected by comparison of the patient medical image with reference medical images that are known not to contain abnormalities (i.e., the reference medical images for this step are from healthy subjects).

Subsequently, a feature extraction may be performed on each detected abnormal image region in order to characterize each abnormality in a multi-dimensional feature space. The multi-dimensional feature space may include, for example, size, surface area, location, eccentricity, orientation, density, and various luminance and contrast parameters. In one or more embodiments of the invention, one complete set of parameters of the multi-dimensional feature space is identified for each detected abnormality.

Additionally or alternatively, the abnormal image region may be manually identified in Step 202 by a medical professional (e.g., X-ray technician). This medical professional (e.g., X-ray technician) may be different from the medical professional (e.g., physician) that inspects/examines the patient medical image to perform a diagnosis.

Figure 2B:
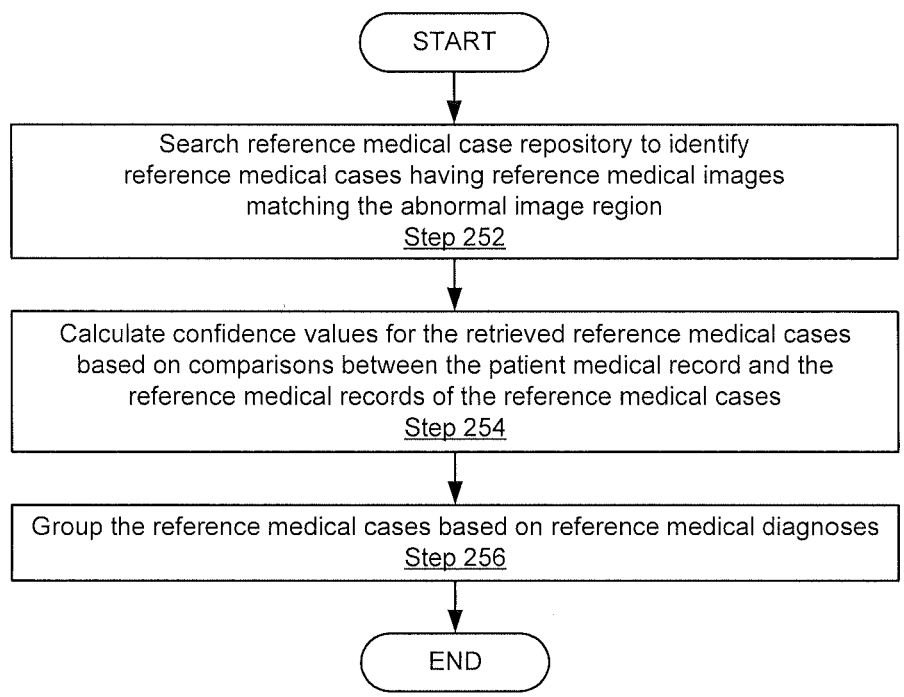

In Step 204, reference medical cases that include reference medical images matching the abnormal image region in the patient medical image are retrieved. FIG. 2B provides additional details regarding Step 204.

In Step 206, the patient medical image and the retrieved reference medical cases are displayed to the user. In one or more embodiments of the invention, the detected abnormalities may be highlighted in the displayed medical image. Further, the cardinality of the identified abnormal image regions (i.e., the number of abnormalities detected in the patient medical image) may be displayed. In one or more embodiments of the invention, the retrieved reference medical cases, displayed to the user, may be grouped by the affiliated reference medical diagnoses. The GUI displaying the reference medical cases to the user may initially summarize the grouped medical cases by displaying only the reference medical diagnoses affiliated with the groups. The user may access the reference medical cases in a group by selecting the group. In one or more embodiments of the invention, the user may browse the reference medical images and the reference medical records. The user may, for example, zoom into the reference medical image and/or the user may request, via the GUI, to display additional details of the reference medical record. Further, the GUI may display, the confidence value (discussed below) calculated for each reference case to indicate the degree of similarity between the patient medical case and the reference medical case. The displayed confidence value may be normalized for a range between 0 and 1, 0% to 100%, etc.

In Step 208, a determination is made about whether the user has manually identified a new abnormal image region. A new abnormal image region may be manually identified by a user (i.e., medical professional) by tracing, using a cursor, the perimeter of the abnormal image region in the patient medical image.

Those skilled in the art, having the benefit of this detailed description, will appreciate that the new abnormal image region may be an image region the user considers abnormal, and might not have been detected as an abnormal image region in Step 202. Further, the new abnormal image region may effectively be any region of interest (ROI), selected by the user. If the user has identified a new abnormal image region, the process returns to Step 204 and Steps 204 and 206 are repeated for the new abnormal image region identified by the user.

Those skilled in the art, having the benefit of this detailed description, will appreciate that Step 202 and the first execution of Step 204 may take place before the patient medical image is shown to the user for inspection/examination. Any subsequent execution of Step 204 is based on new abnormal image regions that were manually identified by the user during examination/inspection of the patient medical image. The steps of manually identifying a new abnormal image region, and subsequently executing Steps 204 and 206 may be repeated any number of times until the user is satisfied with the reference medical cases retrieved in Step 206.

In Step 210, the user may further request additional reference medical cases (i.e., reference cases that were not part of the original set selected for display) to be displayed. Additional reference cases may be, for example, reference cases with diagnoses similar to the reference case currently being reviewed by the user. After selection of the additional reference medical case, the GUI may display the additional reference medical image and the additional reference medical record associated with the additional reference medical case. In one or more embodiments of the invention, the user may continue selecting and reviewing additional reference medical cases until she determines a best-matching reference medical case, i.e., a reference medical case that, in her opinion, is the most suitable for diagnosing the patient medical case.

FIG. 2B shows a flowchart in accordance with one or more embodiments of the invention. The process depicted in FIG. 2B may be used to retrieve, from a reference medical case repository, reference medical cases. Specifically, the process depicted in FIG. 2B may correspond to Step 204, discussed above in reference to FIG. 2A and may be performed by the components of the system (102), discussed above in reference to FIG. 1. In one or more embodiments of the invention, one or more of the steps shown in FIG. 2B may be omitted, repeated, and/or performed in a different order than the order shown in FIG. 2B. Accordingly, the scope of the invention should not be considered limited to the specific arrangement of steps shown in FIG. 2B.

In Step 252, the reference medical case repository is searched for reference medical cases having reference medical images matching the abnormal image region. In other words, the abnormal image region is used as a search criterion. A matching reference medical image may be determined as follows: The reference medical image may be analyzed in the same multi-dimensional feature space that is used to characterize the abnormalities in the patient medical image, as previously described in Step 202. The steps to obtain a characterization of the reference medical image using this multi-dimensional feature space may be performed at run time or in response to a search request for matching reference medical images. Additionally or alternatively, in order accelerate the identification of matching reference medical images, the parameters of the multi-dimensional feature space may have been computed a priori for all reference medical images in the reference medical case repository. In one or more embodiments of the invention, the matching process maps a comparison between the abnormal image region and a reference medical image in $R^N$ feature space to a single value (i.e. $R^1$ space), where the single value reflects the proximity (i.e., the degree of similarity) between the abnormal image region in the patient medical image and the reference medical image. If the single value satisfies a threshold (e.g., the single value is less than the threshold), the reference medical image is deemed to be a match with the abnormal image region. Possible mapping schemes include a weighted distance algorithm, a lookup table, or a non-linear transformation such as an artificial neural network. The weights and/or transformations applied may be obtained via supervised learning if an expert supervisor is available, or via unsupervised learning, based on properties of a large data set. Furthermore, the weights and/or transformations may be adjusted based on users' selections over time, either based on an individual basis (e.g., preference learning), or based on a population basis (e.g., using semi-supervised learning of consensus).

In one or more embodiments of the invention, any reference medical case that includes a reference medical image with at least one abnormality similar to the abnormality detected in the patient medical image may be considered a related reference case and may be selected for further processing.

In Step 254, a similarity analysis is performed for the patient medical case and the reference medical cases retrieved in Step 252. In one or more embodiments of the invention, the similarity analysis may include a comparison of the detected abnormalities in the patient medical image with the abnormalities found in the reference medical images. The similarities of the patient medical image and the reference medical images may be assessed, for example, based on the overlap of the multi-dimensional feature spaces that describe the abnormal image region(s) in the patient medical image and in the reference medical images. The similarity analysis may further include a comparison of the patient medical record with the reference medical records. Factors that are known to be diagnostically relevant may be considered. These factors may include, for example, age, sex, race and other demographic information, and may include other factors such as clinical information and history, drug use, etc. If, for example, a patient medical image is examined for abnormalities that may indicate ovarian cancer, all reference medical cases where the reference medical record indicates that the subject was male would be eliminated. Accordingly, the similarity analysis may weight different factors differently, depending on their diagnostic relevance. In order to quantify similarity, the reference case identification engine may use a scoring process to calculate and assign a confidence value to each reference medical case identified in Step 206, based on the degree of similarity between patient medical case and reference medical case. Higher confidence values may indicate a higher degree of similarity, whereas lower confidence values may indicate a lesser degree of similarity.

In one or more embodiments of the invention, the scoring process may be updated based on the user's selection of the best-matching reference medical case in Step 210, in order to improve future content based image retrieval. In one or more embodiments of the invention, the best-matching reference medical case selected by the user may not be the reference medical case with the highest confidence value. Based on the user's reference medical case browsing history and best-matching reference medical case selection, the system may update the scoring process used to assign confidence values to the reference medical cases. The scoring process may be updated such that the final user-selected reference case receives the highest confidence value when the process of automatically retrieving reference medical images is repeated. The updating of the scoring process may be performed for a particular user of the system, or for the entire user base of the system.

In Step 256, the reference medical cases retrieved in Step 206 are grouped based on their associated reference medical diagnoses. Each group corresponds to a different reference medical diagnosis and may include all retrieved reference medical cases with the particular reference medical diagnosis. The reference medical cases in each group may be sorted based on the confidence values assigned to the reference medical cases in Step 208. A group may contain only a limited number of reference medical cases with a particular reference medical diagnosis (e.g., only the reference medical cases with the top 5 confidence values may be included). Alternatively, a group may contain all reference medical cases with a particular reference medical diagnosis. A group does contain at least one medical case with a particular medical diagnosis.

Figure 3A:
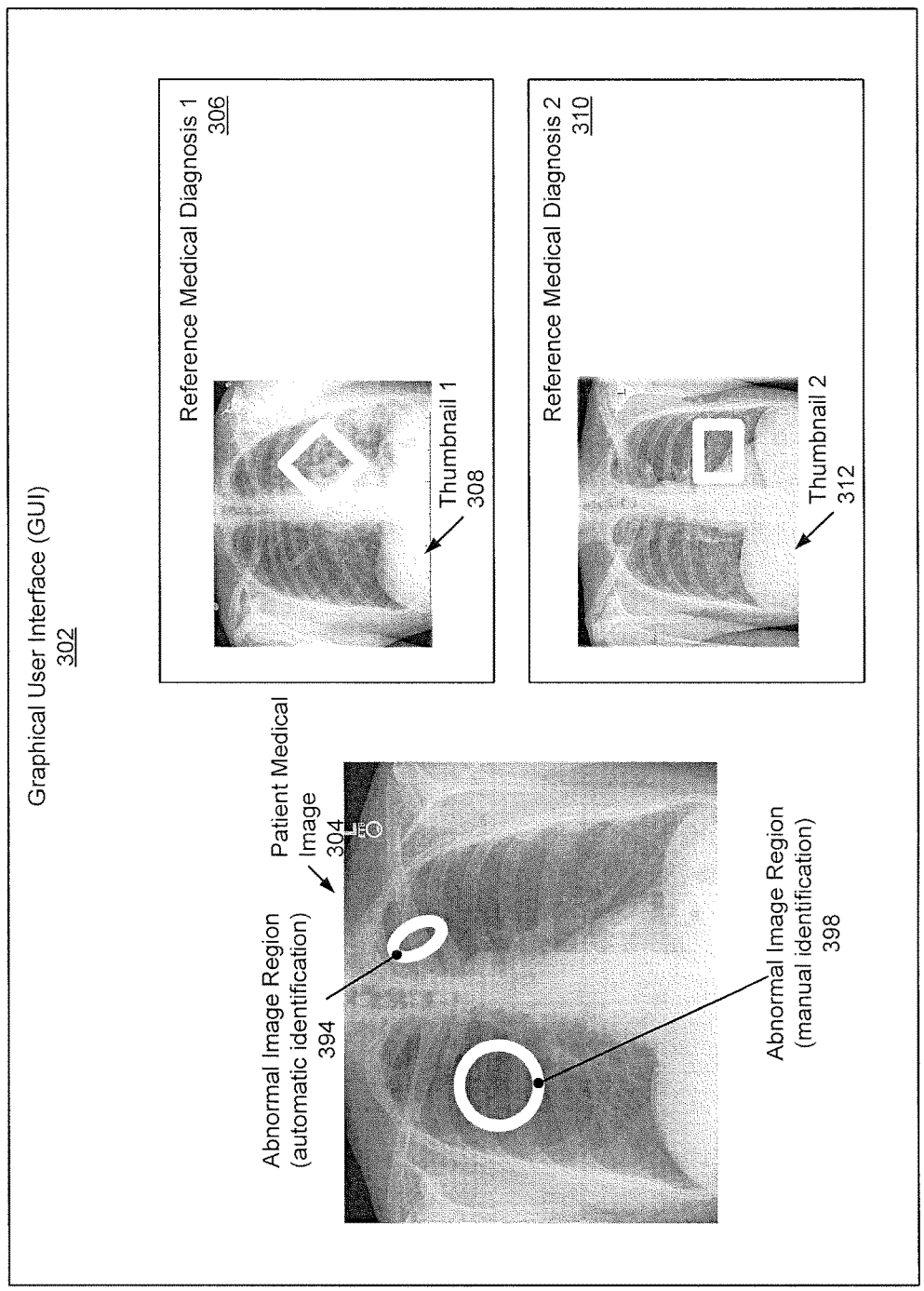
FIGS. 3A and 3B show examples in accordance with one or more embodiments of the invention.
Figure 3B:
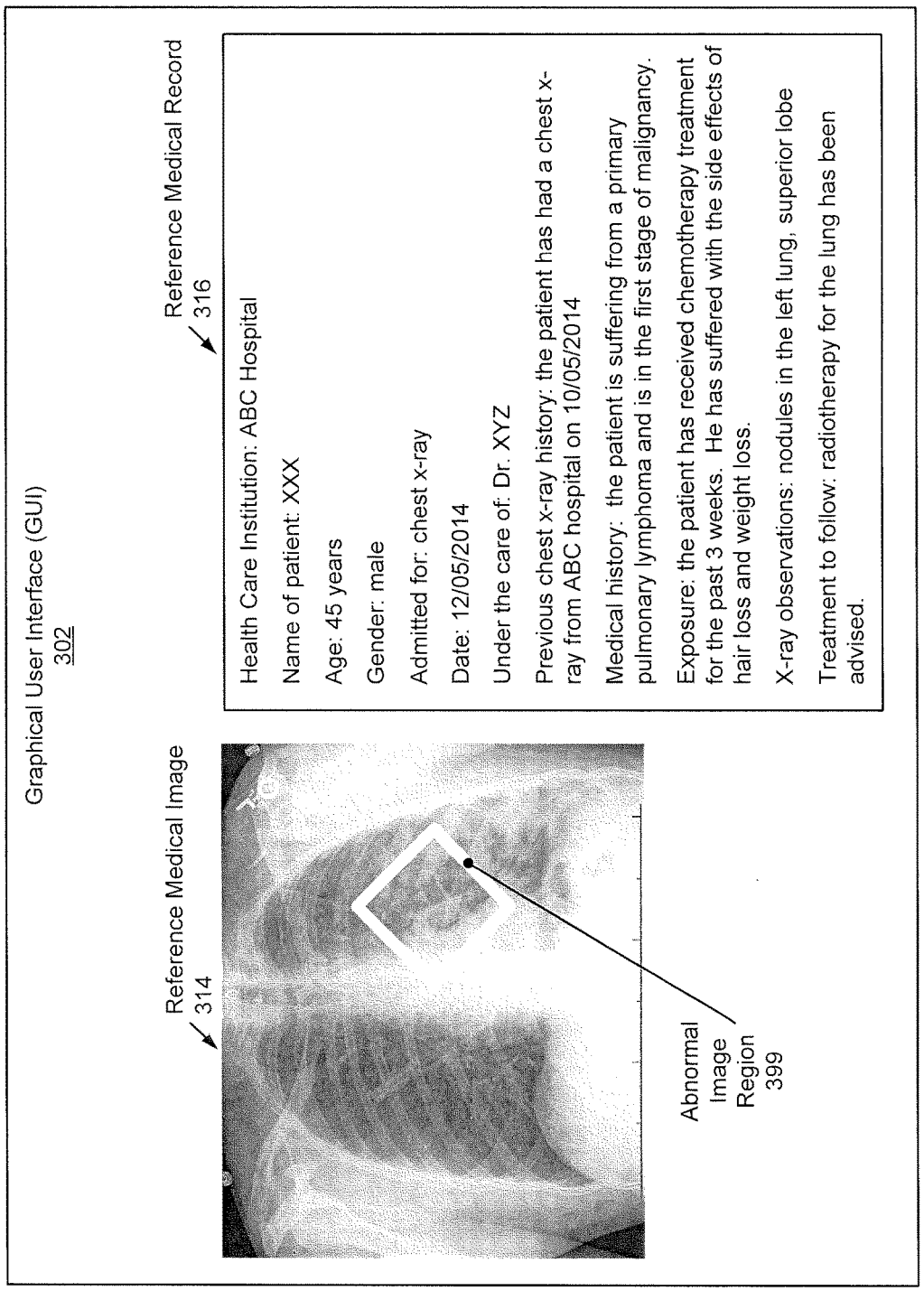

FIGS. 3A and 3B show examples in accordance with one or more embodiments of the invention. The examples shown in FIGS. 3A and 3B are based on a patient medical case that includes a patient medical record and a patient medical image that is an X-ray image of the patient's chest. Accordingly, the reference images of the reference medical cases in the reference medical repository are X-ray images of other, prior patients. The patient medical image contains abnormalities. In the example, the abnormalities are nodules in the patient's lung. Accordingly, the reference medical case repository used in the examples includes reference medical cases with reference medical images that are X-ray images of lungs with nodules. The reference medical cases in the reference medical case repository include reference medical records and reference medical diagnoses. The reference medical case repository includes reference medical cases that comprehensively cover multiple diagnoses that may be affiliated with lung nodules.

In the example, the abnormality (i.e., the nodules in the patient's lung) is detected, and subsequently reference medical cases, organized by diagnosis, are proposed based on the detected abnormality. FIGS. 3A and 3B show screenshots of content displayed by the GUI (302) to the user (e.g., a medical professional interacting with the GUI). FIG. 3A shows a screenshot of the GUI (302) displaying the patient medical image (304) being analyzed and two reference medical diagnoses (306, 310) of reference medical cases matching the patient medical case. FIG. 3B shows a screenshot of the GUI displaying a reference medical case selected by the user. The reference medical case includes a reference medical image (314) and a reference medical record (316).

In FIG. 3A, assume a patient medical image (304) has been obtained using an X-ray machine. Prior to displaying the patient medical image (304) to the physician, an abnormal image region (394) is automatically detected (i.e., using one or more image processing algorithms) within the patient medical image (304). Also prior to displaying the patient medical image (304) to the physician, multiple reference medical cases having reference medical images matching the abnormal image region (394) are retrieved. When the patient medical image (304) is finally displayed to the physician in a GUI (302), the automatically detected abnormal image region (394) is highlighted within the patient medical image (304) and some of the retrieved medical cases are also displayed.

Now assume the physician wishes to examiner/investigate a different abnormal image region (393) within the patient medical image (304). Moreover, unlike the abnormal image region (394), assume this different abnormal image region (393) was not automatically detected. Accordingly, the physician manually identifies/selects the abnormal image region (394). In response to this manual selection, multiple reference medical cases having reference medical images matching the abnormal image region (393) are retrieved and scored. Moreover, the retrieved reference medical cases are grouped according to diagnosis (i.e., each group corresponds to a different medical diagnosis). The GUI (302) displays the reference medical cases grouped by reference medical diagnoses. In the example, there are two groups: one group is affiliated with reference medical diagnosis 1 (306), and one group is affiliated with reference medical diagnosis 2 (310), that are displayed to the user. Thumbnail images (308, 312) are shown for each group. The thumbnail images may be reduced-size versions of the reference medical images of the reference medical cases with the highest confidence value in their groups, or they may be generic images used for the diagnoses affiliated with the groups.

FIG. 3B shows a screenshot of the GUI after the user has selected medical diagnosis 1 (306) for further review. Accordingly, the GUI displays a reference medical image (314) and a reference medical record (316) belonging to a reference medical case affiliated with reference medical diagnosis 1 (306). The reference medical image (314) includes the highlighted abnormal image region (399). The displayed reference medical case may be the reference medical case with the highest confidence value in the group. Subsequently, the user may access the other reference medical cases in the group and review the other reference medical cases' reference medical images and reference medical records, and/or the user may choose to examine the reference medical cases under reference medical diagnosis 2 (310).

Various embodiments of the invention have one or more of the following advantages: the ability to automatically identify abnormalities in a patient medical image before the medical professional examines the patient medical image (increasing the efficiency of the medical professional); the ability to display the patient medical image with the detected abnormalities highlighted; the ability to automatically identify, before the medical professional examines the patient medical image, reference medical cases that are similar to the patient medical case (increasing the efficiency of the medical professional); the ability to automatically select a set of reference medical cases for presentation to a medical professional; the ability to display the selected reference medical cases to a medical professional and enable the medical professional to navigate through the selected reference medical cases having reference medical images and reference medical records; the ability for a medical professional to manually select a region of interest (e.g., abnormal image region) in the displayed patient medical image and repeat the search of the reference medical case repository for reference medical cases based on the manually selected region of interest; the ability to display additional reference medical cases manually selected by the user; and the ability to quantify the similarity between the patient medical case and a reference medical case using a confidence value.

Figure 4:
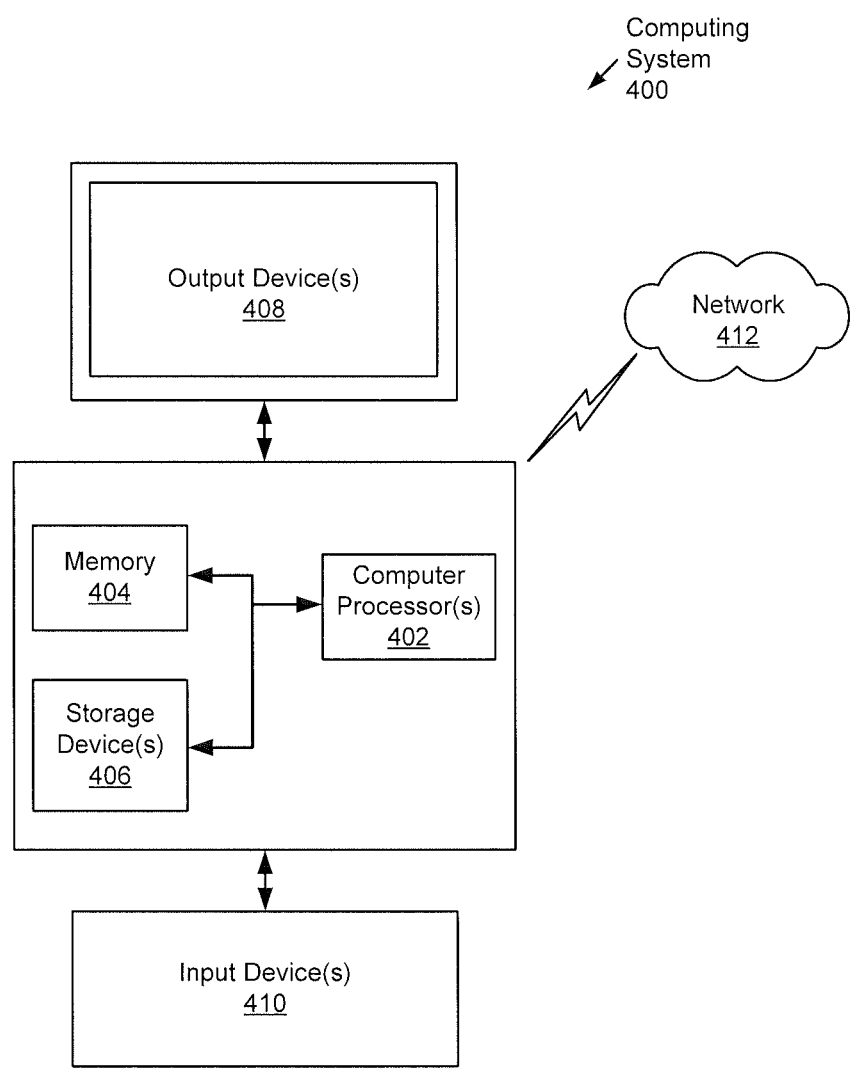
FIG. 4 shows a computer system in accordance with one or more embodiments of the invention.

Embodiments of the invention may be implemented on virtually any type of computing system, regardless of the platform being used. For example, the computing system may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments of the invention. For example, as shown in FIG. 4, the computing system (400) may include one or more computer processor(s) (402), associated memory (404) (e.g., random access memory (RAM), cache memory, flash memory, etc.), one or more storage device(s) (406) (e.g., a hard disk, an optical drive such as a compact disk (CD) drive or digital versatile disk (DVD) drive, a flash memory stick, etc.), and numerous other elements and functionalities. The computer processor(s) (402) may be an integrated circuit for processing instructions. For example, the computer processor(s) may be one or more cores, or micro-cores of a processor. The computing system (400) may also include one or more input device(s) (410), such as a touchscreen, keyboard, mouse, microphone, touchpad, electronic pen, or any other type of input device. Further, the computing system (400) may include one or more output device(s) (408), such as a screen (e.g., a liquid crystal display (LCD), a plasma display, touchscreen, cathode ray tube (CRT) monitor, projector, or other display device), a printer, external storage, or any other output device. One or more of the output device(s) may be the same as or different from the input device(s). The computing system (400) may be connected to a network (412) (e.g., a local area network (LAN), a wide area network (WAN) such as the Internet, mobile network, or any other type of network) via a network interface connection (not shown). The input and output device(s) may be locally or remotely (e.g., via the network (412)) connected to the computer processor(s) (402), memory (404), and storage device(s) (406). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments of the invention.

Further, one or more elements of the aforementioned computing system (400) may be located at a remote location and connected to the other elements over a network (412). Further, one or more embodiments of the invention may be implemented on a distributed system having a plurality of nodes, where each portion of the invention may be located on a different node within the distributed system. In one embodiment of the invention, the node corresponds to a distinct computing device. Alternatively, the node may correspond to a computer processor with associated physical memory. The node may alternatively correspond to a computer processor or micro-core of a computer processor with shared memory and/or resources.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for managing a patient medical case, comprising:
   identifying, by a processor using processed image data and independent of a user input, at least one of a first abnormal image region within a patient medical image of the patient medical case;
   retrieving, by the processor, from a reference medical case repository in a memory and before the patient medical image is displayed, a first plurality of reference medical cases comprising a first plurality of reference medical images matching the first abnormal image region;
   displaying, within a graphical user interface (GUI) screen, the patient medical image and at least one of the first plurality of reference medical cases;
   receiving, via the GUI screen, from a first input device and after the patient medical image is displayed, a trace on the patient medical image that identifies a second abnormal image region within the patient medical image;
   retrieving, by the processor, from the reference medical case repository, a second plurality of reference medical cases comprising a second plurality of reference medical images matching the second abnormal image region; and
   displaying, within the GUI screen, at least one of the second plurality of reference medical cases.

2. The method of claim 1, wherein the first abnormal image region is identified from a second input device.

3. The method of claim 1, further comprising:
   calculating, by the processor using a scoring process, a plurality of confidence values for the second plurality of medical cases based on comparisons between the patient medical case and the second plurality of reference medical cases; and
   grouping, by the processor, the second plurality of reference medical cases into a plurality of groups according to medical diagnoses,
   wherein each of the plurality of groups corresponds to a different medical diagnosis, and
   wherein displaying at least one of the second plurality of reference medical cases comprises displaying at least one reference medical case from each of the plurality of groups.

4. The method of claim 3, further comprising:
   displaying, within the GUI screen, a confidence value for each reference medical case of the second plurality of reference medical cases.

5. The method of claim 3, further comprising:
   receiving, via the GUI screen from the first input device, a selection of a reference medical case of the second plurality of reference medical cases;
   updating, by the processor, the scoring process based on the reference medical case; and
   storing, by the processor, the updated scores in the memory.

6. The method of claim 1, further comprising:
   identifying a plurality of abnormal image regions in the patient medical image;
   displaying, within the GUI screen, a cardinality of the plurality of abnormal image regions.

7. The method of claim 1, further comprising:
   highlighting, within the GUI screen, the first abnormal image region.

8. The method of claim 1, further comprising:
   receiving, via the GUI screen from the first input device, a selection of a reference medical case of the second plurality of reference medical cases; and
   displaying, within the GUI screen and in response to the selection of the reference medical case, the reference medical image and the reference medical record of the reference medical case.

9. The method of claim 8, further comprising:
   receiving, via the GUI screen from the first input device, a selection of an additional reference medical case from the reference medical case repository,
   wherein the additional reference medical case and the reference medical case both have the same medical diagnosis; and
   displaying, within the GUI screen and in response to the selection of the additional reference medical case, an additional reference medical image and an additional reference medical record of the additional reference medical case.

10. A non-transitory computer readable medium (CRM) storing instructions executed by a processor for managing a patient medical case, the instructions comprising functionality for:
   identifying, using processed image data and independent of a user input, at least one of a first abnormal image region within a patient medical image of the patient medical case;
   retrieving, from a reference medical case repository in a memory and before the patient medical image is displayed, a first plurality of reference medical cases comprising a first plurality of reference medical images matching the first abnormal image region;

displaying, within a graphical user interface (GUI) screen, the patient medical image and at least one of the first plurality of reference medical cases;

receiving, from the first input device and after the patient medical image is displayed, a trace on the patient medical image that identifies a second abnormal image region within the patient medical image;

retrieving, from the reference medical case repository, a second plurality of reference medical cases comprising a second plurality of reference medical images matching the second abnormal image region; and displaying, with the GUI screen, at least one of the second plurality of reference medical cases.

11. The non-transitory CRM of claim 10, wherein the instructions for managing a patient medical case further comprise functionality for:

calculating, using a scoring process, a plurality of confidence values for the second plurality of medical cases based on comparisons between the patient medical case and the second plurality of reference medical cases; and grouping the second plurality of reference medical cases into a plurality of groups according to medical diagnoses, wherein each of the plurality of groups corresponds to a different medical diagnosis, and wherein displaying at least one of the second plurality of reference medical cases comprises displaying at least one reference medical case from each of the plurality of groups.

12. The non-transitory CRM of claim 10, wherein the instructions for managing a patient medical case further comprise functionality for:

highlighting, within the GUI screen, the first abnormal image region.

13. The non-transitory CRM of claim 10, wherein the instructions for managing a patient medical case further comprise functionality for:

receiving, via the GUI screen from the first input device, a selection of a reference medical case of the second plurality of reference medical cases; and displaying, within the GUI screen and in response to the selection of the reference medical case, the reference medical image and the reference medical record of the reference medical case.

14. The non-transitory CRM of claim 13, wherein the instructions for managing a patient medical case further comprise functionality for:

receiving, via the GUI screen from the first input device, a selection of an additional reference medical case from the reference medical case repository, wherein the additional reference medical case and the reference medical case both have the same medical diagnosis; and displaying, within the GUI screen and in response to the selection of the additional reference medical case, an additional reference medical image and an additional reference medical record of the additional reference medical case.

* * * * *